United States Patent [19]

Coupek et al.

[11] Patent Number: 4,871,675

[45] Date of Patent: Oct. 3, 1989

[54] STORAGE CONTAINER OF SAMPLES FOR ANALYSIS

[76] Inventors: Jiri Coupek, 1580 Kotorska, Praha 4; Stanislav Voza, 20/214 Bradinska, Praha 9; Borivoj Strejc, 13/1361 Lipanska, Ricany u Praha; Zdenka Tomsova, 1 Radhostska, Praha 3, all of Czechoslovakia

[21] Appl. No.: 85,213

[22] Filed: Aug. 13, 1987

Related U.S. Application Data

[63] Continuation of Ser. No. 801,554, Nov. 25, 1985, abandoned.

[30] Foreign Application Priority Data

Nov. 23, 1984 [CS] Czechoslovakia .................... 9001-84

[51] Int. Cl.[4] .......................... B01L 3/00; C12M 1/16

[52] U.S. Cl. ................................ 435/288; 73/864.91; 206/534; 422/101; 422/102; 435/299

[58] Field of Search .................... 422/101, 102, 59–61, 422/69, 70, 86, 88–89; 436/178; 55/485, 502–503, 505, 512; 73/864.51, 864.91; 206/530, 534, 540; 435/4, 288, 299

[56] References Cited

U.S. PATENT DOCUMENTS

| | | | |
|---|---|---|---|
| Re. 27,008 | 6/1966 | Luckey | 436/178 X |
| 2,506,806 | 5/1950 | Metzger | 422/60 X |
| 2,987,175 | 6/1961 | Bottum | 55/503 X |
| 3,545,930 | 12/1970 | Walker et al. | 422/60 X |
| 3,676,073 | 7/1972 | Luckey | 436/178 |
| 3,734,127 | 5/1973 | Williams et al. | 422/103 X |
| 3,965,750 | 6/1976 | Johnson | 73/864.51 |
| 4,046,015 | 9/1977 | Riedl et al. | 73/874.91 |
| 4,062,652 | 12/1977 | Rolfo-Fontana | 422/61 |
| 4,131,544 | 12/1978 | Elahi | 422/88 X |
| 4,402,911 | 9/1983 | Walters | 73/864.51 X |

*Primary Examiner*—Michael S. Marcus
*Assistant Examiner*—Jill Johnston
*Attorney, Agent, or Firm*—Klein & Vibber

[57] ABSTRACT

A storage container of samples for analysis is disclosed, having a cylindrical tube and two fittings adapted for connection with a syringe, mutual connection of containers in series, or closing and manufactured from a suitable plastic or glass. A column of sorbent is closed at both ends with a porous partition, screen, paper filter, or a layer of silicate or glass wool. The size of sorbent particles is 20–150 um (micrometers). The content of the storage container is protected during storage and/or transportation by closures from both sides. The sorbents which are packed into the storage container are selected from silica gel or organic copolymeric carriers of specific or nonspecific functional groups, which are purposefully chosen. The container finds application in general and clinical analyses, toxicology, environmental protection, agriculture, food industry, biology and biotechnologies for entrapment, storage, preparation and processing of real samples after withdrawing from a source and before the proper analytical determination. The design of the container substantially reduces the time of sample processing and the manufacturing requirements for material and labor.

6 Claims, 1 Drawing Sheet

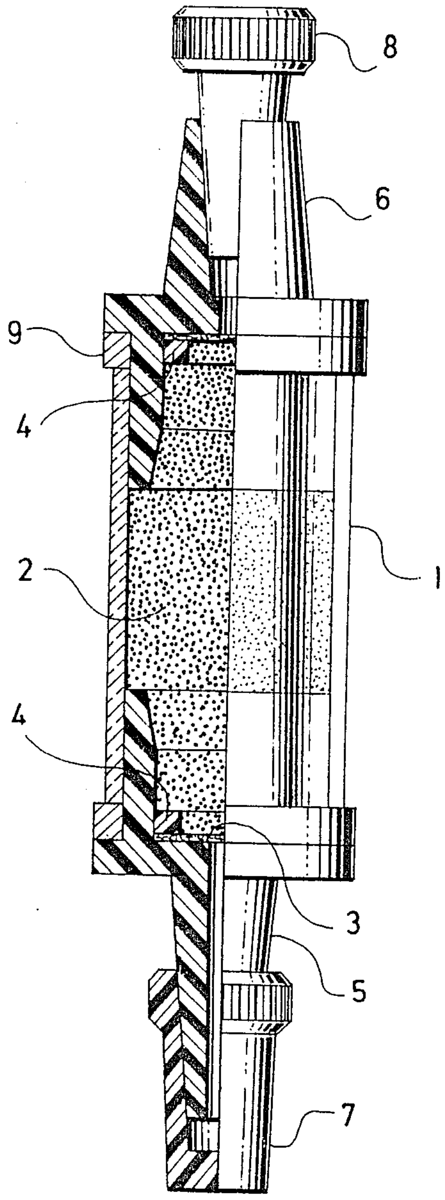
8
6
9
4
2
1
4
3
5
7

STORAGE CONTAINER OF SAMPLES FOR ANALYSIS

This is a continuation of application Ser. No. 801,554, filed 11/25/85, now abandoned.

BACKGROUND OF THE INVENTION

The invention pertains to storage containers in general and, more particularly, a container for samples which serves for entrapping, storage, transportation and processing of a system of analyzed compounds from withdrawal of each sample from its source until the actual analytical determinations. The storage container, according to the invention, can be employed for general chemical and clinical analyses; in toxicology; for environmental inspections; in water analyses; in agriculture; the foods industry; analyses of biologic samples and in biotechnology.

The storage and transportation of samples before analysis, as well as methods for the isolation of a system of compounds for a final analysis, represent a considerable problem requiring a great deal of the total alloted time for determination from the viewpoint of technique and method. It is, therefore, an imperative demand of each modern method of determination to reduce the time necessary for chemical, radiochemical or instrumental analysis, since the periods required for the determination of quantities of investigated components in a properly prepared sample are minutes to tens of minutes.

The commonly employed methods of sample processing, which are based upon extraction techniques and the subsequent concentration of the mixture by evaporation of solvents, require large quantities of pure solvents, laboratory glassware and energy, and are very labor-intensive in general. Also, the transportation of withdrawn samples in an original state from the place of sample taking to the place of analysis can be time consuming and costly, with the further problem that the composition of the sample may change while it is being transported. Mention may be made, by way of example, of special analyses of urine samples, which are carried out in only a few specialized laboratories in large towns of Czechoslovakia, withdrawing and determination of trace contaminants in waste or surface waters, and withdrawing and determination of radioactive or highly toxic materials from fields.

A critical evaluation of time and expense for a single analytical determination in a real sample reveals that a final analysis by means of a modern instrumental technique is less time consuming and less expensive than the previously known operations for entrapping, storage, transportation and processing of samples. Relatively little attention has been given to this problem, which represents a genuine need in the art, and which is now solved by means of the present invention.

In comparison with the known extraction methods, the technique of sorption on the solid surface of a sorbent presents numerous advantages, above all for the determination of very small concentrations of investigated compounds, where a perfect purity of extraction agents plays a decisive role, with regard to the volumes applied, in the potential for contamination of the sample during its preparation. A known system in the United States for concentration of compounds is SepPac® of Waters Co., which consists in utilization of a radially compressible plastic material for preparation of tubes containing a solid sorbent. A disadvantage of this known process, however, is the relatively expensive special plastic material the production of which requires a special processing technology. This fact is reflected in the relatively high price of the product. Other disadvantages relative to the object of the present invention are the hydrodynamic conditions during entrapment of a sample in the tube and its desorption, and also the danger of a subsequent contamination of absorbed sample through open inlet and outlet means of the tubes during long storage periods. Moreover, the choice of sorption materials is limited to two fundamental sorbents in the known system. Similar characteristics are associated with the concentration precolumn and sorbents produced by Merck Co., FRG, under the trade name Extrelut®.

It is, therefore, an object according to the present invention to provide a fast and inexpensive technique for sample determinations, free from the defects and disadvantages of the known techniques.

SUMMARY OF THE INVENTION

This object is attained according to the present invention by a storage container of samples for analysis, which serves for entrapment, storage, and transportation of a very broad scope of compounds, and includes a cylindrical tube (1) (see FIG. 1) made from a plastic material and packed with a sorbent (2), and two plastic fittings (5) and (6), which contain a porous partition (3) from poly (tetrafluoroethylene), polypropylene, poly (vinyl chloride), or polyurethane, or a screen from a metal, glass, polyamide, polyester, or poly (tetrafluoroethylene) fabric, paper, or a layer of glass or silicate wool. The porous partition is fixed with a ring (4). One of the plastic fittings (5) has a conical outlet, whereas another one (6) of the plastic fittings is provided with a conical opening of the same taper, which enables connection to a syringe, connection of the storage containers of samples in series, or the sealing thereof with plastic closures (7,8). The cylindrical tube, fittings, and closures are made from a plastic material selected from polyethylene, polypropylene, fluorinated polyolefins, poly (vinyl chloride), polyamide, and polystyrene, or from glass. The type of sorbent is indicated by color rings (9).

The storage container of samples in accordance with the present invention may be packed with various sorbents depending upon the intended purpose. These involve above all the nonspecifically absorbing materials for general-purpose application such as e.g. silica gel and its $C_1$–$C_8$ alkyl, cyano, amino or alkylamino derivatives, and organic macroporous spherical materials of a copolymer type, either unmodified or alkylated. A greater selectivity is achieved with sorbents carrying ionogenic functional groups $—NR_3$, $—NR_2$, $—SO_3^-$, $—COO^-$, and $OPO_3^{2-}$ on an inorganic or organic macroporous matrix. Highly selective sorbents, which contain immobilized affinity ligands, for example, covalently bonded enzymes, enzyme inhibitors, antidotes, or antigens or synthetic ligands, have special applications. This type of sorbent in the storage container of samples, according to the present invention, has a highly prospective application in sets for analytical determinations, i.e. mainly in clinical analyses (determination of hormones, bile acids, cytostatics and their metabolites, drugs, etc.), environmental inspection, agriculture, the food industry, biology and biotechnologies (determination of vitamins, saccharides, pesticides, carcinogens, etc., and also of enzymes, inhibitors, etc.).

In comparison with the known techniques and systems for entrapment, storage, processing or transportation of samples, the storage container of samples, according to the present invention, is marked by substantially lower time and cost demands with regard to the user. Moreover, its manufacture is easier and consequently less expensive. The storage container of samples is designed exclusively from rotation parts, which fact facilitates the preparation of pressing molds and enables mass production and complete automation of assembly.

An important advantage is the possibility of storing a sample in the container for a long time and in a comfortable transportation with respect to the shape, small dimensions, and the means for closing the container. The avoided consumption of solvents and reagents, and a broad variablility with regard to the possibilities for application of the storage container, are further merits. Noteworthy is a high degree of reproducibility and yield of the sample desorption with the storage container, characteristics that have been proven by tests of repeated use. Economic reasons can easily be given for single use of the container in entrapment and storage of radioactive and highly toxic compounds.

The invention is further illustrated and documented in examples, which, however, do not limit its scope by any means.

BRIEF DESCRIPTION OF THE DRAWINGS

The sole FIGURE is a front upright view in partial cross-section of the storage container in accordance with the present invention.

DESCRIPTION OF THE PREFERRED EMBODIMENTS

EXAMPLE 1

A storage container of samples was made from polypropylene in the form shown in FIG. 1, where reference numeral (1) represents a tube, (2) a sorbent, (3) a porous partition, (4) a ring, (5) and (6) plastic fittings, and (7) and (8) stoppers. The volume of the container is 1.5 ml and the length is 40 mm . The container has a screen (3) of poly (tetrafluoroethylene) (20 μm mesh) fixed in both fittings. It is packed with 350 mg spherical silica-gel sorbent of particle size 50–80 μm, carrying a covalently bonded $C_{18}$ phase (SEPARON $C_{18}$®). The container is washed before application by forcing through it 5 ml methanol and 5 ml water, after which 2 ml urine are forced through by means of pressure from a syringe. Next, the container is again washed, with 5 ml distilled water. The container is then closed and stored, or transported to the place of analysis.

Before the final analysis, the container is opened, a syringe is set into the upper opening, and the absorbed sample is eluted with 2 ml methanol.

The described procedure is used for routine analyses of steroid hormones in urine. The analytical terminal procedure is gas chromatography, radioimmunoassay and thin-layer chromatography. The analytical recovery is determined for 24 steroids and amounts to, on the average, 33% higher in comparison to the common isolation of these compounds from urine by known extraction techniques. The time for sample processing decreased with the storage containers of samples according to the present invention to 5–10% of the time expended with the known extraction techniques.

EXAMPLE 2

The storage container of samples, according to Example 1, is manufactured from poly (vinyl chloride), and its fittings are furnished with a polyamide fabric of mesh diameter 15 um, fixed with a poly (tetrafluoroethylene) ring, instead of the poly-(tetrafluoroethylene) screens. The container is used for entrapment and storage of a model sample of radioactively labeled steroids from blood plasma in an amount of about 4 ng in 5 ml. The following recoveries are obtained: cortisol 95%, estradiol 94%, testosterone 92%, 18-OH-DOC 89%, and androstenedione 90%.

EXAMPLE 3

A storage container of samples having the same dimensions as that of Example 1 is made from polyethylene, packed with the $C_{18}$ derivative of silica gel (SEPARON $C_{18}$®) of particle size 80–120 μm. The sorbent column is closed with a poly(tetrafluoroethylene) ring and a poly(tetrafluoroethylene) fabric and used for entrapment and storage of digitalin glycosides from an extract of rabbit adrenal glands. Thin-layer chromatography proved entrapment of 11 compounds of this type and the method compared favorably with the standard extraction technique.

EXAMPLE 4

A storage container of samples made from poly(-vinylidene fluoride) and having the same dimensions as in Example 1 is packed with spherical macroporous particles of a styrene-ethylene dimethacrylate copolymer (SEPARON SE®) of particle size 32–40 μm. The column is closed with a glass fabric and a poly(tetrafluoroethylene) ring. The container is used for entrapment of aromatic hydrocarbons from 200 ml water containing 20–150 ng of coronene, anthrathrene, dibenzo-fluoranthrene, ophenylenepyrene, benzo(a)chrysene, perylene, benzo(a)pyrene, fluoranthrene and anthracene in 1 ml water. The desorption is performed after a three-week's storage of the sample in the closed container with 2 ml of a mixture of ethanol-ether (1:1). The recovery ranges from 93 to 100%. The compounds are determined by spectrofluorimetry.

EXAMPLE 5

A storage container of samples according to Example 4 consists of a vessel made from polyamide with spherical silica gel having a covalently bonded phase (SEPARON SIX $C_{18}$®) of particle size 20–50 μm as sorbent. The column of sorbent is closed with stainless-steel screens of mesh size 5 μm. The entrapped sample and the employed desorption system are analogous to those of Example 4. The recovery ranges from 90 to 100%.

EXAMPLE 6

The storage container of samples according to Example 1, with the only difference being that the cylindrical part is made from glass and the fittings and stoppers from poly(tetrafluoroethylene) is packed with a spherical copolymer of 2-hydroxyethyl methacrylate with ethylene dimethacrylate having an exclusion limit of molecular weight $10^6$ daltons, and covalently bonded specific inhibitor of pepsine (ε-aminocaproyl-L-Phe-D-Phe-OMe) in an amount 0.5 μmol/g of the carrier, the particle size being 100–200 μm. Entrapment and washing of the sample from a pepsine containing extract of Aspergillus oryzae is carried out from a 0.1 M solution of sodium acetate. The container is closed and stored for 48 hours at temperature of 4° C. The desorption is performed with 0.1M sodium acetate solution of pH 4.5 containing 1M NaCl. Example 6 demonstrates an application of the storage container of samples in a biospecific sorption.

EXAMPLE 7

The storage container of samples, according to Example 1, is packed with the spherical macroporous cation exchanger SEPARON 300 P ® (a copolymer of 2-hydroxyethyl methacrylate with ethylene dimethacrylate carrying covalently bonded functional groups —$OPO_3^{2-}$; exclusion limit of molecular weight 300,000 daltons, capacity 3.0 mequiv/g, particle size 20–60 μm). The column is closed with a partition from porous poly(tetrafluoroethylene) fixed with a poly(tetrafluoroethylene) ring. Entrapment of cellulolytic enzymes from a cultivation liquor Trichoderma viride-resei is carried out from a 0.005 M solution of sodium acetate (pH 4). The sample is stored for 72 hours at 4° C. without losing its activity, and the desorption is performed with a sodium acetate solution containing 3 M NaCl. This example illustrates the utilization of storage containers, according to the invention, packed with a macroporous cation exchanger.

EXAMPLE 8

A storage container of samples of volume capacity 2.5 ml and made from poly(vinyl chloride) is packed with an anion exchanger SEPARON 1000 DEAE ® (a copolymer of 2-hydroxyethyl methacrylate with ethylene dimethacrylate carrying covalently bonded diethyleminoethyl functional groups, exchange capacity 2.05 mequiv/g, particle size 20–40 μm). The column is closed from both sides with a porous poly(vinyl chloride). Entrapment of a mixture of proteins from human blood serum is carried out from the solution in a buffer (0.025 M phosphoric acid+Tris, pH 8.5). The container is washed with the same buffer, stored at 4° C. for 48 hours, followed by elution of the absorbed proteins with the buffer 0.5 phosphoric acid+Tris+1 M NaCl (pH 3.2) and analysis. This example demonstrates utilization of the storage container of samples, according to the present invention, packed with a macroporous anion exchanger.

Although the invention is described and illustrated with reference to a plurality of embodiments thereof, it is to be expressly understood that it is in no way limited to the disclosure of such preferred embodiments but is capable of numerous modifications within the scope of the appended claims.

We claim:

1. A storage container for storing samples before analysis comprising a cylindrical tube made from plastic or glass and packed with a sorbent, two plastic fittings, each said two plastic fittings being disposed at an opposite end of said cylindrical tube, said two plastic fittings defining openings into said cylindrical tube, one of said two plastic fittings defining a conically widening portion and the other of said two plastic fittings defines a conically narrowing portion of the same taper, thereby allowing connection of said container to a syringe, connection of a plurality of said containers in series, or closing of said container by closure means, wherein said sorbent has a particle size in the range from 20 to 150 um and is selected from the group consisting of high purity polymeric macroporous silicon dioxide and $C_1$–$C_{18}$ alkyl, CN, $NH_2$, $NR_3$, $NR_2$ and $SO_3$ derivatives, wherein R is an alkyl group, and macroporous organic polymers with particles of vertical shape carrying immobilized selective functional groups selected from the group consisting of enzymes, inhibitors of enzymes, and antigens, or carrying the covalently bonded nonselective functional groups selected from the group consisting of $C_1$ to $C_{18}$ alkyls, $NR_3$, $NR_2$, $SO_3$, $OPO_3^-$, and $COO^-$, wherein R is an alkyl group.

2. The storage container according to claim 1, further comprising closure means, said closure means adapted to be fitted to said conical portions of said plastic fittings, wherein said cylindrical tube, said two plastic fittings and said closure means are made from plastics selected from the group consisting of polyethylene, fluorinated polyolefins, polypropylene, polyamide, polystryrene and poly(vinyl chloride).

3. The storage container according to claim 1, further comprising said two plastic fittings accommodating partition means, wherein said partition means is a porous partition made from polyethylene, polypropylene, poly(tetrafluoroethylene), poly(vinyl chloride) or polyurethane.

4. The storage container according to claim 1, further comprising said two plastic fittings accommodating partition means, wherein said partition means is a screen made from a metal glass, poly(tetrafluoroethylene), polyamide, or polyester fabric.

5. The storage container according to claim 1, further comprising said two plastic fittings accommodating partition means, wherein said partition means comprise a paper filter.

6. The storage container for analysis of samples according to claim 1, further comprising said two plastic fittings accommodating partition means, wherein said partition means comprise a layer of glass or silicate wool.

* * * * *